United States Patent [19]

Hoppe et al.

[11] Patent Number: 4,747,687
[45] Date of Patent: May 31, 1988

[54] BALL CELL WINDOWS FOR SPECTROPHOTOMETERS

[75] Inventors: Thomas Hoppe; Miner Munk, both of Palm Beach, Fla.

[73] Assignee: Milton Roy Company, St. Petersburg, Fla.

[21] Appl. No.: 898,730

[22] Filed: Aug. 14, 1986

Related U.S. Application Data

[63] Continuation of Ser. No. 618,560, Jun. 8, 1984, abandoned.

[51] Int. Cl.[4] ...................... G01N 21/05; G01N 21/85
[52] U.S. Cl. ...................................... 356/246; 356/410
[58] Field of Search ............... 356/246, 410, 411, 440; 250/373

[56] References Cited

U.S. PATENT DOCUMENTS 3,497,303  2/1970  Enemark et al. .................... 356/246
3,614,452  10/1971  Felton .................................. 356/410
3,970,388  7/1976  Hacker ................................. 356/246
4,192,614  3/1980  DeMay et al. .

OTHER PUBLICATIONS

James P. S. Southall, "Mirrors, Prisms and Lenses", 1964, p. 396, Proudct Design and Development, Mar. 1984, p. 3.

Primary Examiner—Vincent P. McGraw
Assistant Examiner—S. A. Turner
Attorney, Agent, or Firm—Woodcock Washburn Kurtz Mackiewicz & Norris

[57] ABSTRACT

A detector cell assembly for spectrophotometry has a radiation transparent spherical ball closing the opening in a cell body through which radiation passes. The spherical ball is of fused silica or sapphire and is pressed the cell body in a direct seal. The radiation has a crossed ray pattern within the cell.

7 Claims, 10 Drawing Sheets

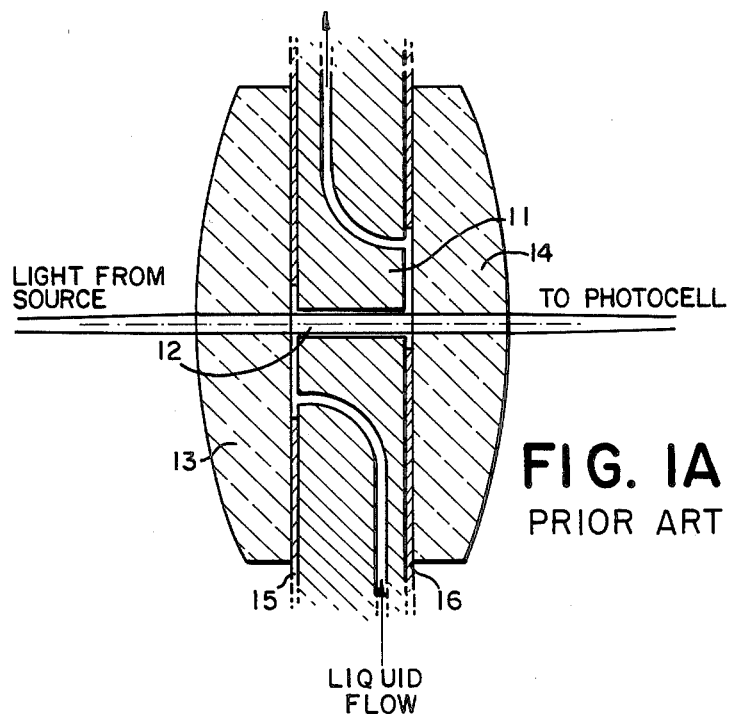
FIG. IA
PRIOR ART
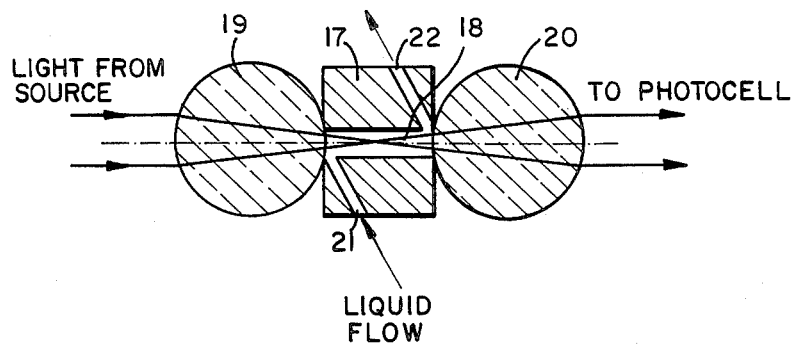
FIG. I

BALL CELL WINDOWS FOR SPECTROPHOTOMETERS

This is a continuation, of application Ser. No. 618,560, filed June 8, 1984, now abandoned.

FIELD OF THE INVENTION

The present invention relates to detectors for spectrophotometry and more particularly, to a spherical ball window sealing a sample cell.

BACKGROUND OF THE INVENTION

In spectrophotometry, radiation from a source passes through a sample cell to a photodetector which measures the amount of radiation absorbed by the sample fluid in the cell. The output of the detector is a measure of absorbence of a particular wavelength of radiation. The quantitative presence of certain materials in the sample is identified by particular wavelengths characteristically absorbed by the materials. An important use of spectrophotometric detectors is in chromatography wherein the components of a chromatographic column are separated in a column and the radiation absorbence of the separated components are then measured by a spectrophotometric detector.

In such detectors, radiation transparent optical windows allow radiation from the source to pass through the cell to the detector. In a common spectrophotometric detector, radiation passes through an entrance window, through the cell in a direction parallel to the flow of sample fluid through the cell, and through an exit window to the detector. Flat windows or plano convex lenses typically have been used. U.S. Pat. No. 4,192,614-deMey, et al shows a detector assembly with flat windows at the entrance and exit openings in the cell. A lens focuses the radiation in a pattern which converges in the cell.

Another type of commonly used detector has divergent optics with sample fluid flow across a substantially planar radiation field in the cell. Such crossflow cells are typified by the Milton Roy LDC microcell used in conjunction with the LDC Model 1204D spectroMonitor detector. Crossflow cells permit close coupling of the cell to the outlet end of a chromatographic column, but these cells are limited in available pathlength. Parallel flow cells, where the light rays travel substantially parallel to the direction of fluid flow in the cell, are less limited in available pathlength of light rays in the cell and can provide better sensitivity for sample detection. Crossing of the light rays in the parallel flow cell makes it less sensitive changes in flow rate because the light rays do not graze the lateral walls of the cell where the transverse temperature gradients are largest.

The flat or plano convex windows used in prior art detectors are sealed to the cell body with gaskets having gaps for the passage of radiation through the cell. These gaps contribute significantly to peak spreading in present commercially used detectors at the flow rates encountered in microbore high pressure liquid chromatography (HPLC). Furthermore, the cell body must have a smooth, flat surface for good gasket seals. This has been a perpetual manufacturing problem.

The use of plastic materials in the construction of cell bodies has advantages. Lateral thermal gradients in parallel flow cells make light absorption detectors sensitive to changes in solvent flow rate because of the Schlieren refraction of the light rays as they pass through the cell. One solution to this problem is to construct the cell wall of a thermally insulating material such as plastic so that heat does not flow laterally in the cell, and the lateral thermal gradients are greatly diminished. Cells have been constructed of plastic in the past, but creep of the plastic under the flat cell window surfaces due to sealing pressure often causes the windows to crack. The cracked windows leave indentations in the plastic which hinder further use of the cell body with new windows.

Spherical balls have long been used as optical focusing elements. See "MIRRORS, PRISMS AND LENSES" by James P. S. Southall, Dover Publications, 1964, p. 396. Recently, precision balls have been used for fiber optic coupling. See *Product Design and Development*, March, 1984, p. 3.

Spheres have not been used to form the cell windows in spectrophotometric detectors, possibly because of the short focal lengths of the spheres, and a perceived difficulty in coupling them to the rest of the optics.

It is an object of the present invention to provide a direct glass to metal seal for a spectrophotometric cell with a radiation transparent spherical ball pressed into the optical opening in the cell body.

It is another object of the present invention to produce a convergent ray path in the sample cell with focusing by a spherical ball as the window for the cell.

It is another object of the present invention to provide a window for a detector cell which makes the use of a plastic cell body practical.

It is another object of the present invention to provide a detector cell assembly which is particularly suitable for use in microbore HPLC wherein a chromatographic column can be positioned very closely to the detector cell.

SUMMARY OF THE INVENTION

In accordance with the present invention, a radiation transparent spherical ball closes an opening in a detector cell. Ball termination of the cell offers distinct advantages over flat surface termination. The balls are mechanically stronger than flat windows or plano convex lenses. Sapphire and fused silica balls are available at a reasonable cost. A sapphire ball to metal seal has been pressure checked to 9,000 psi. The troublesome gasket gaps in prior art cells are eliminated with a glass to metal seal.

The spherical geometry of the ball windows is especially strong and does not crack under the normal sealing pressures, so that plastic cell bodies are considerably more practical with ball windows than with the flat surface windows.

The foregoing and other objects, features and advantages of the invention will be better understood from the following more detailed description and appended claims.

SHORT DESCRIPTION OF THE DRAWINGS

FIG. 1A shows a prior art cell with a flat window;

FIG. 1 shows the detector cells assembly of the present invention with spherical ball windows;

DESCRIPTION OF THE PREFERRED EMBODIMENT

Figure 2:
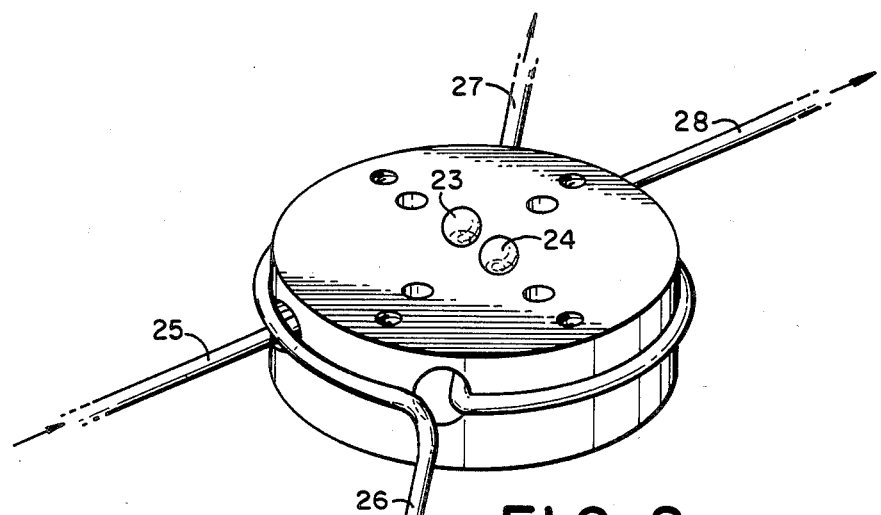
FIG. 2 is a perspective view of the cell body.

FIG. 1A shows a cross-section of the prior art, 1 microleter volume, 3 mm path flow cell of the type used, for example, on Milton Roy LDC Spectromonitor detectors. The cell assembly is positioned between a radiation source and a photodetector. A cell body 11 has a cell 12 for holding a sample on which spectrophotometric measurements are to be made. Plano convex lenses 13 and 14 are sealed to the cell body by gaskets 15 and 16 which have gaps around the cell 12 to permit flow of liquid through the cell and passage of radiation from the source to the detector. Such a cell assembly may have a thin (e.g., ⅛" thick) flow cell body in the region of the gasket seal (e.g., ½" diameter). This presents manufacturing difficulties because of warping of the cell body in the region of the gasket seal. Another problem which has been encountered is peak spreading caused by the unswept regions in the gasket cutouts which provide fluid connection to the bore of the cell and the relatively long inlet channel to the cell.

FIG. 1 shows a cross-section, on the same scale as FIG. 1A, of a spherical ball window in a cell assembly with the same cell dimensions as in FIG. 1A. Cell body 17 has a cell 18 for holding a sample. Radiation transparent spherical balls 19 and 20 close the openings in the cell through which radiation passes as it traverses. Inlet port 21 and outlet port 22 permit sample fluid to flow through the cell parallel to the radiation passing through the cell. The ball 19 focuses the radiation so that the radiation has a crossed ray pattern within the cell. High strength sapphire and fused silica balls permit a direct seal between the cell body and the spherical ball window without the use of gaskets. Sapphire has a higher strength than fused silica and can be employed in an extremely high pressure seal. However, fused silica has adequate strengths for the pressure seal required in most applications. Further, fused silica has a lower refractive index (approximately 1.5 as opposed to approximately 1.8 for sapphire) which provides focusing further into the cell as will be apparent from the subsequently discussed examples.

The small diameter of the balls compared to the flat surface lens permit closer coupling to the cell bore and less peak spreading in the inlet fluid channel. The cost to manufacture the ball window cell is less for at least three reasons. First, balls are less expensive than the plano convex lenses. Secondly, a flat gasket sealing surface is not required. And, thirdly, no gasket is required. In addition, the ball window cell permits high pressure operation.

The direct seal afforded by the present invention is particularly suitable for us with a plastic cell body. Suitable chemically inert plastics include polyphenylene sulfide, one type of which is sold by Valco Instrument Company, Inc. under the tradename VIC 1 and a polyimide resin plastic sold by DuPont under the tradename Vespel ™.

FIG. 2 is a perspective view of an actual cell body which contains both a reference cell and a sample cell. Balls 23 and 24 close the entrance openings of the sample and reference cells. Similar balls on the other side of the cell body close the exit openings. Inlet tubes 25 and 26 and outlet tubes 27 and 28 carry sample and reference fluids to and from the inlet and outlet ports for the sample and reference fluids.

Figure 3:
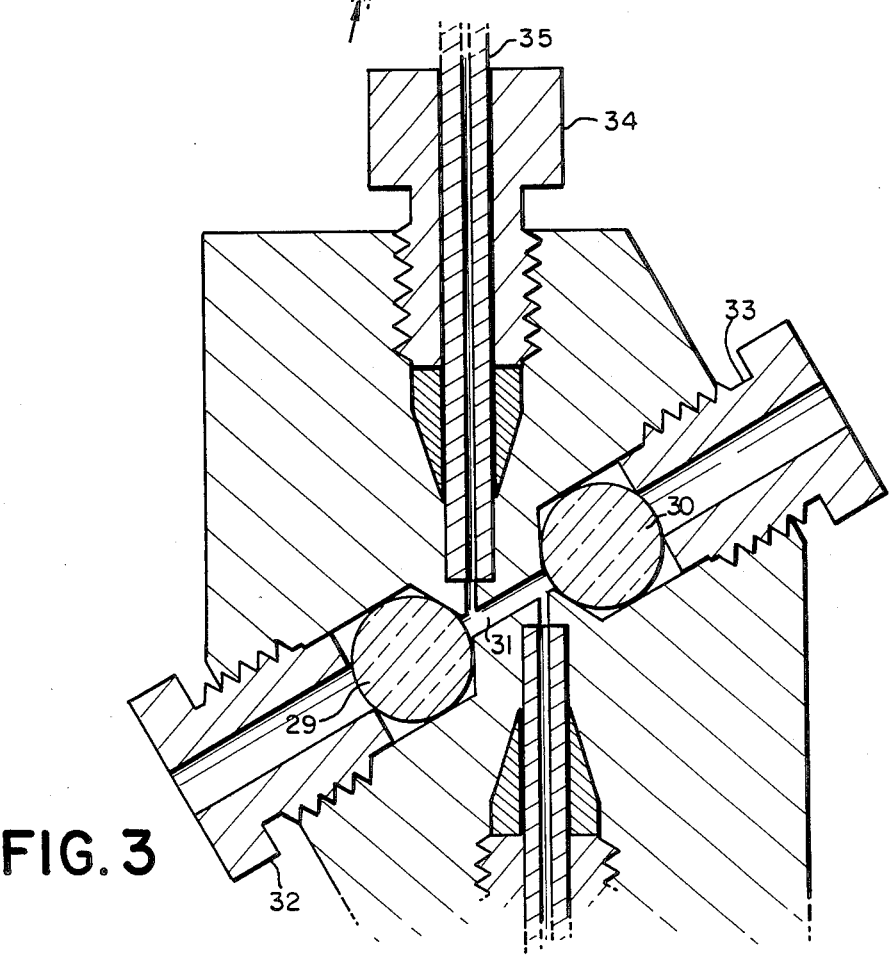
FIG. 3 shows one configuration of the cell and body.

FIG. 3 shows one configuration of a detector cell assembly wherein 4 mm diameter balls 29 and 30 close the openings in a cell which is 0.066 mm diameter by 3 mm long. The cell body has a threaded opening in which the balls reside. Threaded fittings 32 and 33 are screwed into the threaded openings to press the spherical balls 29 and 30 against the cell body in a direct seal. Fittings 32 and 33 have openings for passage of radiation through the cell. A 1/16" compression fitting 34 carries a 1/6" outside diameter by 0.10" inside diameter tubing 35. The tubing carries sample fluid to the inlet port of the cell 31. A similar fitting carries tubing which conveys the sample fluid from the outlet port of the cell.

In a similar configuration, a 4 mm diameter ball closes a cell which is 0.052" by 10 mm long. FIG. 3, and the variation just described, provide the cell dimensions of currently used 1 microleter and 13.7 microleter flow cells.

Figure 4:
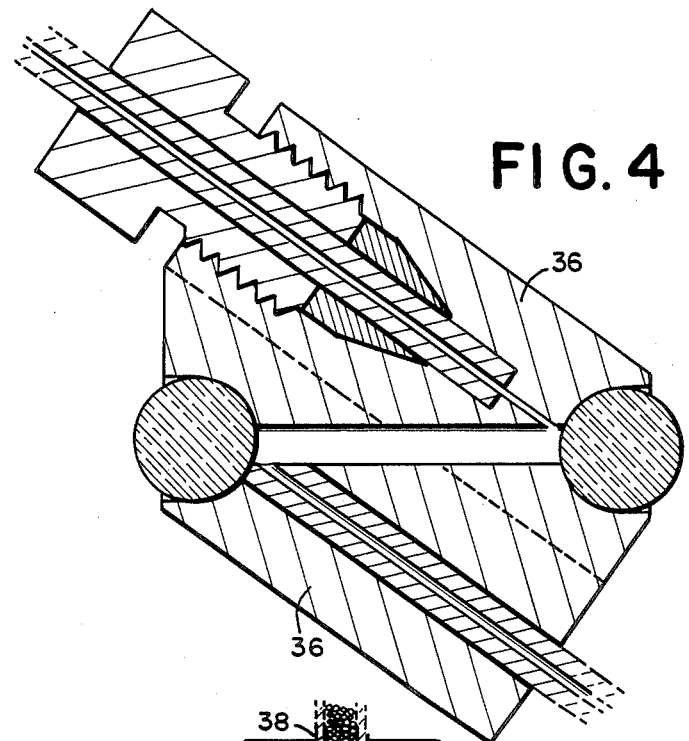
FIG. 4 is another variation of the cell body.

FIG. 4 shows an alternative cell body construction wherein two pieces 36 and 37 of ¼" hexbar or square cross-section bar are brazed together and drilled through a 35° angle to form the cell. The flow channels to the cell are either machined-in fittings or brazed-in tubes.

Figure 5:
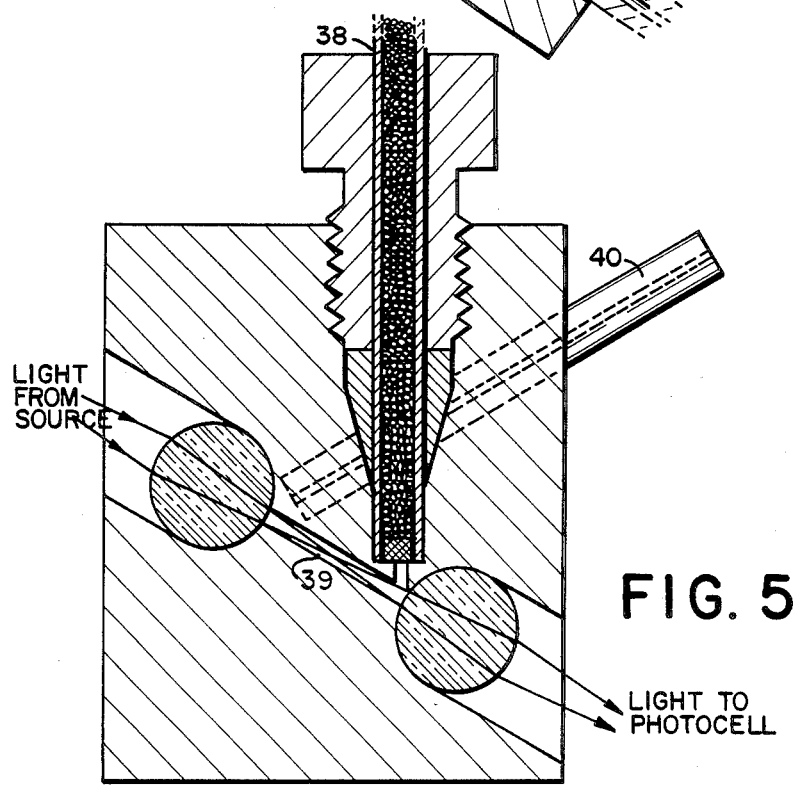
FIG. 5 shows the cell in a microbore HPLC system.
Figure 6:
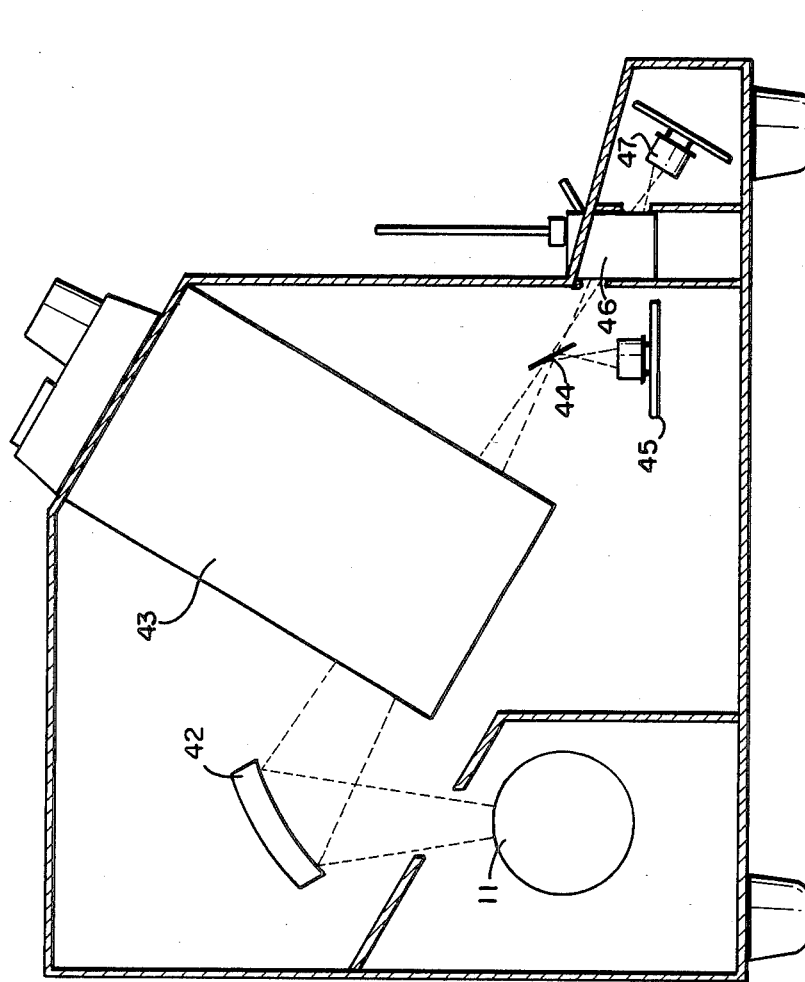
FIG. 6 shows the chromatographic measuring system.
Figure 7:
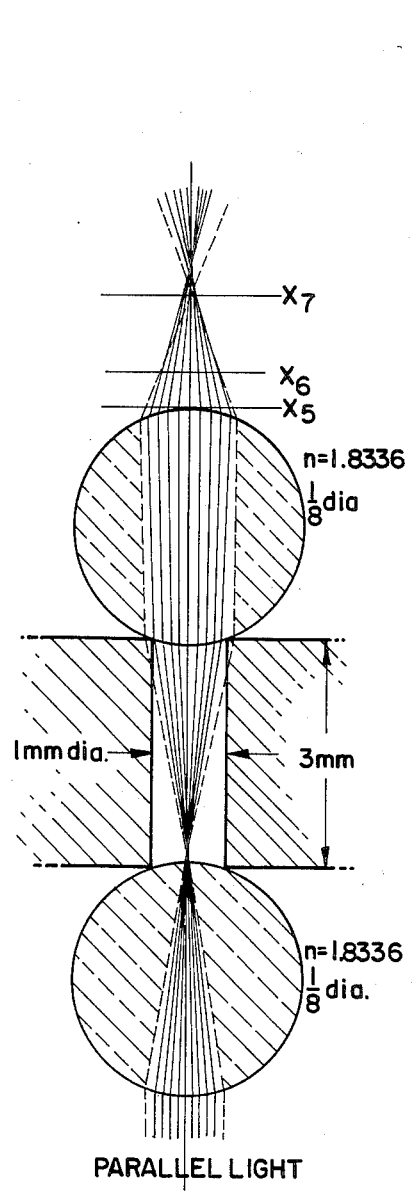
FIGS. 7–13 depict the ray paths in different examples of the invention.
Figure 8:
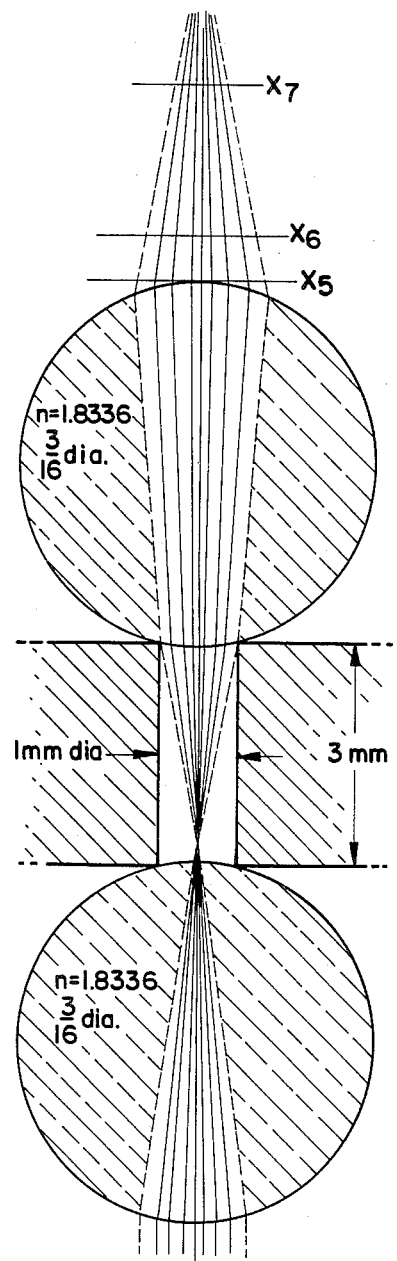
Figure 9:
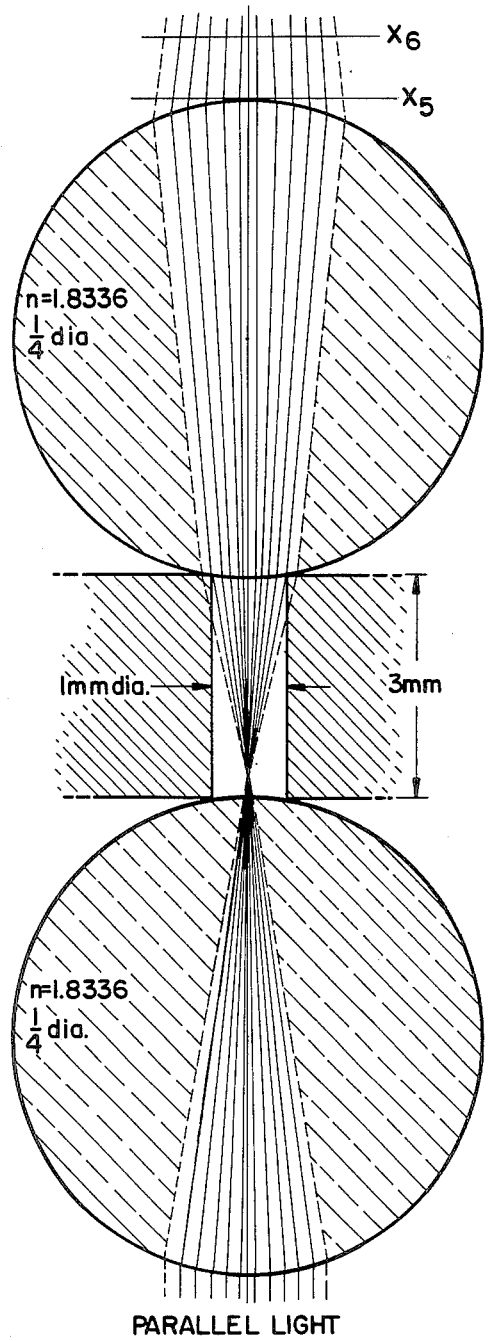
Figure 10:
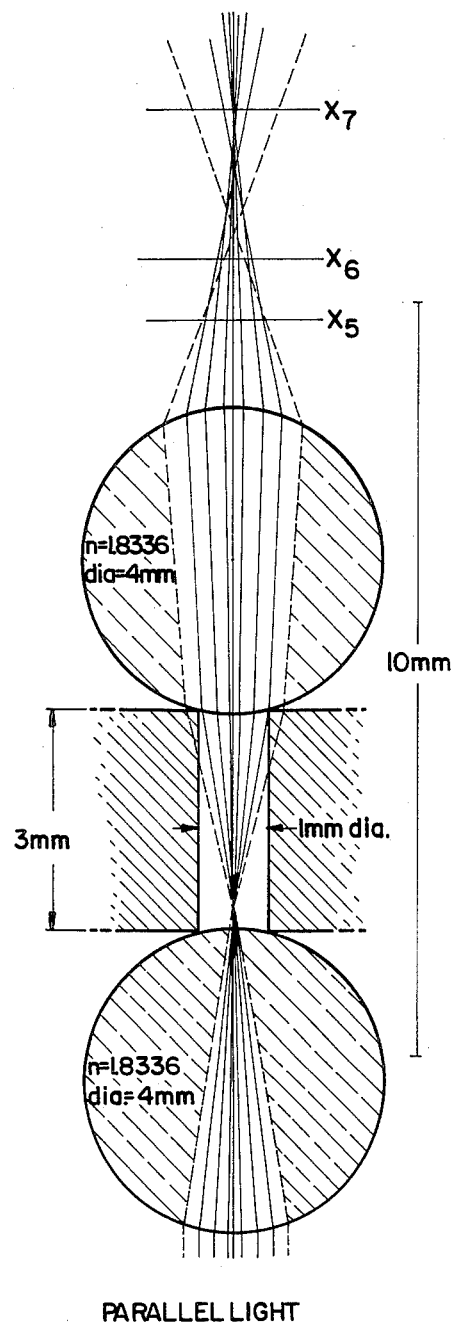

FIG. 5 shows a detector cell assembly with a cell which is close coupled to a microbore HPLC column 38. The chromatographic column 38 terminates adjacent to an opening at the bottom of the cell 39, so that fluid chromatographically separated in the column can be directly transferred to the cell for spectrophotometric measurements. Flow through the cell and outlet tube 40 is uphill to clear bubbles. This type of cell design is incorporated in a compact variable wavelength detector shown in FIG. 6. In FIG. 6, radiation from deuterium lamp 41 is reflected by concave mirror 42 through the filter 43 to the beam splitter 44. Part of the radiation passes to the reference photocell 45 and part of the radiation passes through the flow cell 46 of the present invention. A sample photocell 47 detects the radiation after passing through the sample cell. Chromatographic column 48 separates the sample into components which are measured for absorbence at different wavelengths.

EXAMPLES

Because of the geometrical simplicity of spheres, the light rays can be traced through the cell by direct application of Snell's law at the four optical interfaces. A Texas Instruments T159 programmable calculator was programmed to calculate the coordinates of the rays at the four optical interfaces and at three selectable axial locations past the second ball. In addition, the location of the ray cross over in the cell, the pathlength in the cell, and the point at which the ray crosses the optical axis past the second ball were calculated. The angles of incidence and refraction at the four optical interfaces were calculated. These angles can be used to calculate the Fresnel reflection losses at the four interfaces. The program traced rays incident at a prescribed position and angle on the first surface of the first ball so that the effects of an aperture at this point could be evaluated directly. The program calculated where the ray would have crossed the optical axis ahead of the first ball. Data inputs for the program are the two refractive indices of the media outside the balls (normally 1 for air), the refractive indices of the two balls, the refractive index of the liquid in the cell, the diameters of the two balls, the diameter of the cell and the length of the bore.

The program was applied to different ball diameters and cell dimensions for parallel incident light. Five of the examples are for sapphire balls and two are fused silica balls for comparison.

The procedure used to generate ray trace diagrams from the program calculations was to draw to accurate scale the longitudinal section through the balls and the cell bore. The calculated lateral displacement of each ray at the four optical interfaces were made on the scale drawing as well as the lateral displacement at one of the selected axial locations past the second ball. These marks were then connected with straight line segments to construct the ray trace diagram. Ray trace diagrams constructed in this manner are shown in FIGS. 7 through 13. Calculations were made for light incident at the first surface at 0.001° rather than 0° with respect to the optic axis in order to avoid a singularity in the calculation (division by zero.) Except for FIGS. 8 and 12, the set of incident rays were those at ±0.1, ±0.3 . . . mm from the optical axis.

FIGS. 7 through 10 are for ⅛" diameter, 3/16" diameter, ¼" diameter, and 4 mm diameter sapphire balls in 1 mm diameter by 3 mm long cells. The refractive index of sapphire was taken as 1.8336 which corresponds to 265.20 nm, and the refractive index of the liquid was taken as 1.3330 (water) as it was in all seven figures. Rays transmitted through the cell are shown as solid lines, while the dashed lines indicate rays which strike the lateral wall of the cell.

Figure 11:
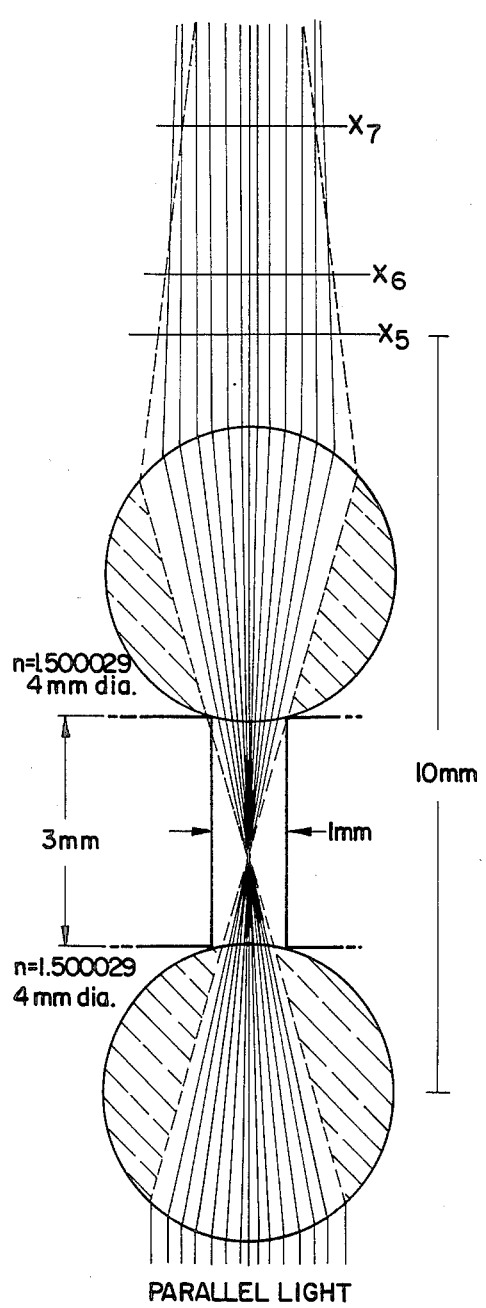
Figure 12:
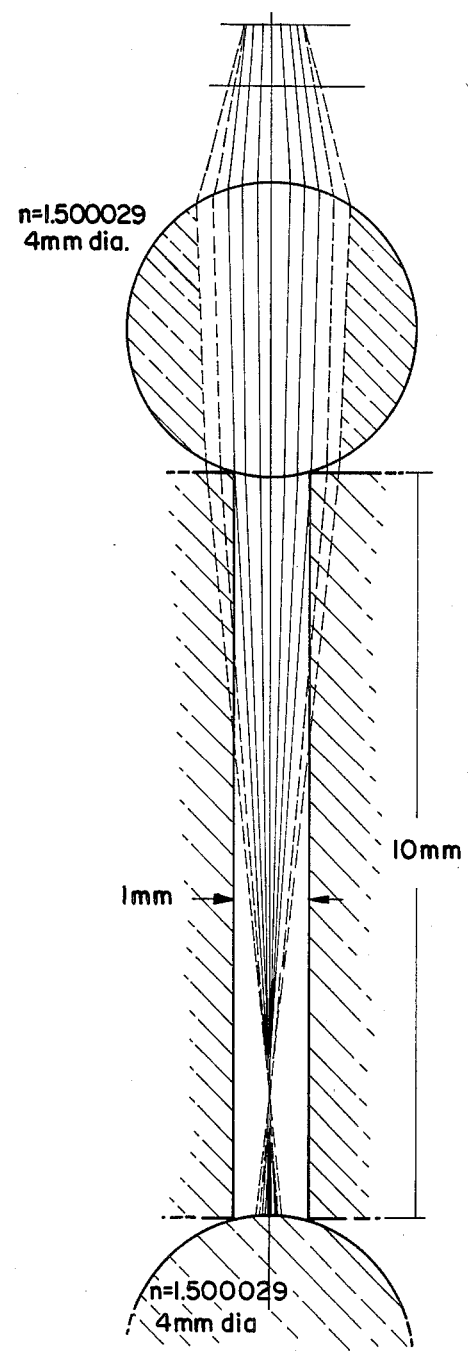

FIGS. 11 and 12 are for 4 mm diameter fused silica balls in 1 mm diameter cells. FIG. 11 is for a bore length of 3 mm, and FIG. 12 is for a bore length of 10 mm. The refractive index of fused silica is taken as 1.500029 which corresponds to a wavelength of 265.20 n.m.

Figure 13:
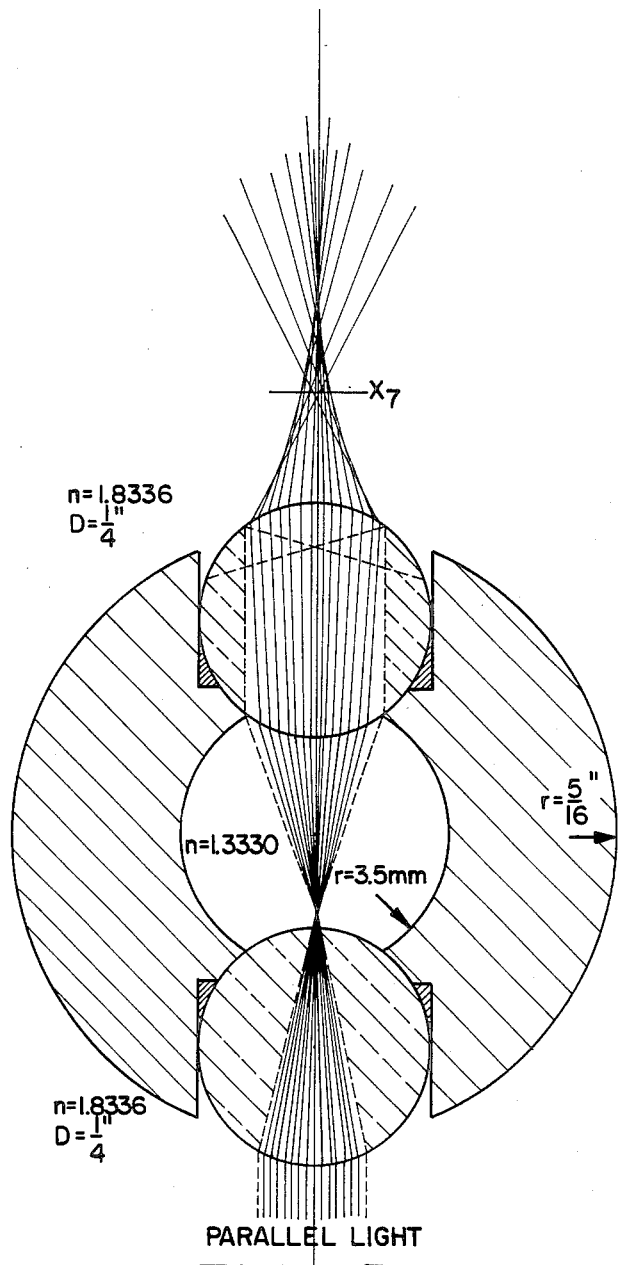

FIG. 13 is for ¼" diameter sapphire balls in a cross flow geometry with a tube diameter of 7 mm and an average pathlength of 5 mm. This particular set of dimensions is suitable for a high pressure super-critical-fluid extraction system monitor.

The differences in pathlength were determined for the different rays in the cell. The pathlengths were calculated for different values of $y_1$, the distance of the incoming ray from the optical axis at the first ball surface. Of the cases shown in FIGS. 7 through 12, the largest difference in ray pathlengths in the cell occurs in the case with 4 mm diameter fused silica balls and a 1 mm diameter by 3 mm long bore cell. The difference in pathlengths in this case is 10.3% and about twice the difference in pathlengths in a 1 mm diameter by 3 mm long cell with flat windows where diagonal transmission occurs in the cell. The increased difference in pathlengths in the ball window cell will cause a slight, but tolerable loss in linearity of response.

Figure 14:
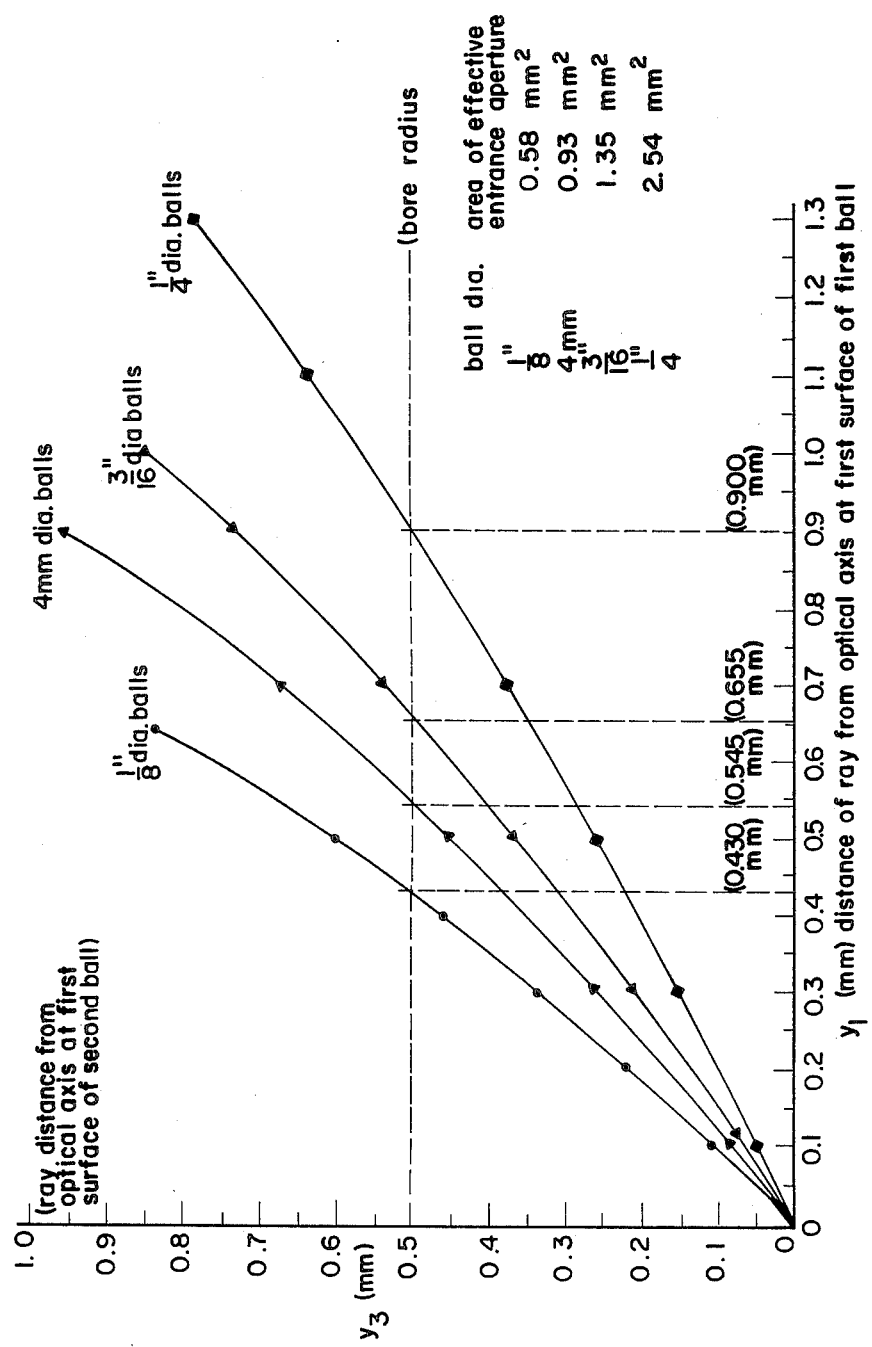
FIGS. 14 and 15 show the effective entrance aperture for different diameter balls of sapphire and fused silica.

A major optical advantage of ball windows over flat windows is the increased effective entrance aperture (entrance pupil) of the cell. The entrance aperture is defined by the light ray which is just transmitted through the cell without striking the cell wall. This limiting ray can be determined by plotting the lateral displacement of the ray at the location of the limiting stop versus the original distance of the ray from the optical axis as done in FIG. 14 for the four diameter sapphire balls in a 1 mm diameter by 3 mm long cell. In this case, the limiting light stop is the trailing rim of the flow cell. The distance of the ray from the optical axis at the first intersection with the second ball ($y_3$) defines the ray's lateral displacement at this axial location. The intersections of the calculated curves in FIG. 14 with a horizontal line at 0.5 mm (radius of the cell) represent the limiting rays. These limiting rays are listed in the following table along with the area they define at the first ball surface.

| | 1 mm dia. × 3 mm long cell | |
|---|---|---|
| sapphire ball diameter | value of $y_1$ for limiting ray | entrance area at first ball surface |
| ⅛" (3.175 mm) | 0.430 mm | 0.58 mm² |
| 4 mm | 0.545 mm | 0.93 mm² |
| 3/16" (4.7625 mm) | 0.655 mm | 1.35 mm² |
| ¼" (6.35 mm) | 0.900 mm | 2.54 mm² |
| flat window | 0.500 mm | 0.78 mm² |

The effective entrance aperture of the cell increases with ball diameter and for the ¼" diameter balls is 3.2 times the area represented by a cell with flat windows. Even the 4 mm diameter balls which can be used with present commercial sample and reference cell spacing give an increase of 19% in effective entrance aperture area in the 1 mm diameter by 3 mm cell with parallel incident light.

Figure 15:
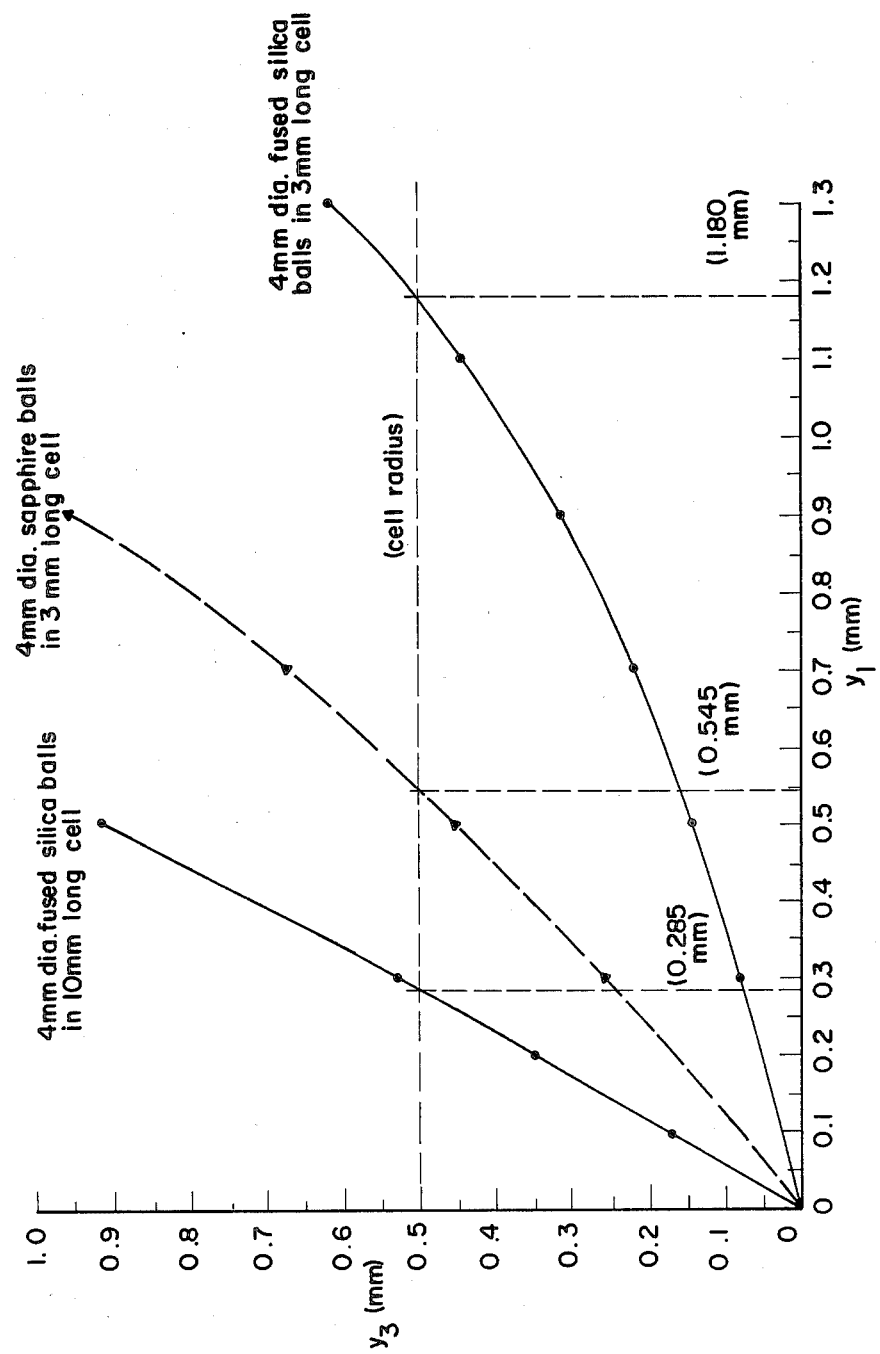

Values of $y_3$ are plotted against $y_1$ values in FIG. 15 for 4 mm diameter fused silica balls in a 1 mm diameter by 3 mm long cell and a 1 mm diameter by 10 mm long cell. The 4 mm diameter sapphire ball curve is repeated from FIG. 14 for comparison (dashed curve). The effective entrance aperture and area is listed for the three cases in the following table.

| | $y_1$ for limiting ray | entrance area at first ball |
|---|---|---|
| fused silica balls in 3 mm long cell | 1.180 mm | 4.37 mm² |
| fused silica balls in 10 mm long cell | 0.285 mm | 0.26 mm² |
| sapphire balls in 3 mm long cell | 0.545 mm | 0.93 mm² |
| flat window | 0.500 mm | 0.78 mm² |

The area of the effective entrance aperture for the 4 mm diameter fused silica balls in the 3 mm long cell is 5.6 times that for flat windows with parallel incident light, and 4.7 times the area of the effective entrance aperture for the 4 mm diameter sapphire balls in the same cell.

A dramatic decrease in area of the entrance aperture occurs when the cell length is increased from 3 mm to 10 mm for parallel incident light. The entrance area for the 4 mm diameter fused silica balls in the 10 mm long cell is about ⅓ that for flat windows. Divergent light illumination will shift the ray cross-over point in the cell toward the trailing end of the cell and increase the effective entrance aperture over that for flat windows.

The ray cross-over within the cell, made practical by the high refractive power of balls, reduces the extent to which rays travel close to the lateral wall of the cell where the transverse temperature gradient is the largest. The transverse temperature gradient is responsible for bending of the light rays in the flow cell, and the flow rate dependence of temperature gradient results in flow sensitivity of the detector.

Flow sensitivity can be reduced further by shifting the ray cross-over point past the center of the cell so that the leading rim of the flow cell becomes the limiting aperture. Then all rays that pass through this rim are transmitted through the cell regardless of their bending by transverse thermal gradients in the cell. This shift in ray cross-over can be achieved with divergent illumination of the cell by moving the light source in from infinity (case with parallel illumination).

While a particular embodiment of the invention has been shown and described, various modifications are within the true spirit and scope of the invention. The appended claims are, therefore, intended to cover all such modifications.

What is claimed is:

1. A detector cell assembly for use in spectrophotometry wherein a source of radiation is spaced from a photodetector with said cell assembly being positioned between the radiation source and the photodetector, said detector cell assembly comprising:
    a body having a sealed cell therein for holding a sample on which spectrophotometric measurements are to be made;
    a first radiation transparent spherical ball closing a first opening in said cell at which radiation enters said cell, said first spherical ball being in a first direct seal with said cell, said first direct seal being capable of withstanding high pressure;
    a second radiation transparent spherical ball closing a second opening in said cell at which radiation exits said cell, said second spherical ball being in a second direct seal with said cell, said second direct seal being capable of withstanding high pressure; and
    wherein said first spherical ball focuses said radiation so that said radiation has a crossed ray pattern within said cell and said second spherical ball directs said radiation to said photodetector for detection.

2. The detector cell assembly recited in claim 1 wherein said cell has inlet and outlet ports for sample fluid which flows through said cell parallel to radiation passing through said cell.

3. The detector cell assembly recited in claim 1 wherein said spherical ball is fused silica.

4. The detector cell assembly recited in claim 1 wherein said spherical ball is sapphire.

5. The detector cell assembly recited in claim 1 wherein said body is a chemically inert plastic material.

6. The cell assembly recited in claim 1 wherein said first and second openings for passage of radiation therethrough are threaded; and said cell assembly further comprises:
    a first and second threaded fitting in said first and second threaded openings, first and second threaded fittings pressing said first and second sperical balls respectively against said cell body in a direct seal.

7. The detector cell assembly recited in claim 1 in a chromatographic measuring system having a chromatographic column which terminates adjacent to an opening in said cell, so that fluid chromatographically separated in said column can be directly transferred to said cell for spectrophotometric measurements.

* * * * *